(12) United States Patent
Cummins et al.

(10) Patent No.: US 10,098,768 B2
(45) Date of Patent: Oct. 16, 2018

(54) RATCHET OPERATED VASCULAR INTERVENTION DEVICE DELIVERY SYSTEM

(71) Applicant: Cook Medical Technologies LLC, Bloomington, IN (US)

(72) Inventors: Sean Cummins, Limerick (IE); Darach McGrath, Tipperary (IE)

(73) Assignee: Cook Medical Technologies LLC, Bloomington, IN (US)

( * ) Notice: Subject to any disclaimer, the term of this patent is extended or adjusted under 35 U.S.C. 154(b) by 293 days.

(21) Appl. No.: 14/799,892

(22) Filed: Jul. 15, 2015

(65) Prior Publication Data

US 2016/0074184 A1 Mar. 17, 2016

Related U.S. Application Data

(60) Provisional application No. 62/050,388, filed on Sep. 15, 2014.

(51) Int. Cl.
*A61F 2/966* (2013.01)
*A61F 2/95* (2013.01)
(Continued)

(52) U.S. Cl.
CPC ............... *A61F 2/95* (2013.01); *A61F 2/844* (2013.01); *A61F 2/962* (2013.01); *A61F 2/966* (2013.01);
(Continued)

(58) Field of Classification Search
CPC ............................. A61F 2/95–2/97; F16H 1/00
(Continued)

(56) References Cited

U.S. PATENT DOCUMENTS

| 844,550 A | * | 2/1907 | Thomasson | ............... A01C 7/18 |
| | | | | 111/16 |
| 1,615,534 A | * | 1/1927 | Cassel | ..................... F16D 41/12 |
| | | | | 123/179.9 |

(Continued)

FOREIGN PATENT DOCUMENTS

EP  2431009  3/2012
JP  2007-97620  4/2007

(Continued)

OTHER PUBLICATIONS

Information Disclosure Statement and Declaration of Darach McGrath Re: ev3 Inc. Stent Delivery System On-Sale Jul. 11, 2013 Prior Art.

*Primary Examiner* — Kathleen Holwerda
(74) *Attorney, Agent, or Firm* — Liell & McNeil

(57) ABSTRACT

A vascular intervention device delivery system, such as for implanting a self expanding stent, includes a thumbwheel rotatably mounted in a handle. The thumbwheel includes a radially outward thumb surface and a radially inward ratchet surface of a ratchet. A catheter has a proximal end attached to the handle, and a distal carrier segment for mounting a vascular intervention device thereon. A retractable sheath is movable from a first position covering the distal carrier segment to a second position retracted proximally uncovering the distal carrier segment. A pull extends between the thumbwheel and the retractable sheath. A ratchet pawl is mounted in the handle and has a catch in contact with the ratchet surface. The ratchet holds the thumbwheel against rotation in a forward direction, and the retractable sheath moves responsive to rotation of the thumbwheel in a reverse direction.

21 Claims, 3 Drawing Sheets

(51) Int. Cl.
*A61F 2/962* (2013.01)
*A61F 2/844* (2013.01)
*A61B 17/00* (2006.01)

(52) U.S. Cl.
CPC ............ *A61B 2017/00407* (2013.01); *A61F 2002/9517* (2013.01); *A61F 2230/0069* (2013.01)

(58) Field of Classification Search
USPC .......... 192/46; 623/1.11–1.54; 606/108, 194
See application file for complete search history.

(56) References Cited

U.S. PATENT DOCUMENTS

| | | | |
|---|---|---|---|
| 3,589,486 A * | 6/1971 | Kelch | F16D 41/18 192/46 |
| 5,088,581 A * | 2/1992 | Duve | F16D 41/12 192/107 M |
| 5,772,669 A | 6/1998 | Vrba | |
| 6,190,360 B1 | 2/2001 | Iancea et al. | |
| 6,238,402 B1 | 5/2001 | Sullivan, III et al. | |
| 6,395,017 B1 * | 5/2002 | Dwyer | A61F 2/962 623/1.11 |
| 7,967,829 B2 | 6/2011 | Gunderson et al. | |
| 7,976,574 B2 | 7/2011 | Papp | |
| 8,337,077 B2 * | 12/2012 | Giacobino | G04B 11/006 368/147 |
| 8,500,789 B2 | 8/2013 | Wuebbeling et al. | |
| 9,901,468 B2 | 2/2018 | Harada | |
| 2005/0149159 A1 | 7/2005 | Andreas et al. | |
| 2005/0273151 A1 | 12/2005 | Fulkerson et al. | |
| 2006/0259124 A1 * | 11/2006 | Matsuoka | A61F 2/966 623/1.12 |
| 2007/0032860 A1 | 2/2007 | Brooks et al. | |
| 2007/0055342 A1 | 3/2007 | Wu et al. | |
| 2007/0088421 A1 | 4/2007 | Loewen | |
| 2007/0156225 A1 | 7/2007 | George et al. | |
| 2007/0168014 A1 | 7/2007 | Jimenez et al. | |
| 2008/0091257 A1 | 4/2008 | Andreas et al. | |
| 2009/0210046 A1 | 8/2009 | Shumer et al. | |
| 2010/0004606 A1 | 1/2010 | Hansen et al. | |
| 2010/0174290 A1 * | 7/2010 | Wuebbeling | A61F 2/95 606/108 |
| 2011/0299366 A1 | 12/2011 | Giacobino | |
| 2012/0041537 A1 | 2/2012 | Parker et al. | |
| 2012/0059448 A1 | 3/2012 | Parker et al. | |
| 2012/0101562 A1 | 4/2012 | Gunderson et al. | |
| 2012/0123516 A1 | 5/2012 | Gerdts et al. | |
| 2012/0158120 A1 | 6/2012 | Hacker et al. | |
| 2012/0330401 A1 | 12/2012 | Sugimoto et al. | |
| 2013/0013047 A1 | 1/2013 | Ramos et al. | |
| 2013/0018451 A1 | 1/2013 | Grabowski et al. | |
| 2013/0110223 A1 | 5/2013 | Munsinger et al. | |
| 2014/0188209 A1 | 7/2014 | Loewen | |
| 2015/0297378 A1 * | 10/2015 | Senness | A61F 2/95 623/1.11 |

FOREIGN PATENT DOCUMENTS

| | | |
|---|---|---|
| WO | 9717899 | 5/1997 |
| WO | 2008034793 | 3/2008 |

\* cited by examiner

RATCHET OPERATED VASCULAR INTERVENTION DEVICE DELIVERY SYSTEM

TECHNICAL FIELD

The present disclosure relates generally to vascular intervention device delivery systems, and more particularly to a feature that holds the thumbwheel against rotation in one direction, but permits rotation in an opposite direction for deployment of a vascular intervention device.

BACKGROUND

Self expanding stents and similar vascular intervention devices are often delivered and deployed using so called pin and pull systems. Typically, the stent is compressed between a retractable outer sheath and an inner catheter. To deploy the stent, the user has to pull the outer sheath to uncover the stent using one hand while resisting the force with the other hand on the inner catheter to maintain the position of the stent during deployment. In pin and pull systems, the user can have difficultly maintaining the inner catheter at a fixed position while simultaneously moving the outer sheath. In very difficult stent deployments, which require a large amount of force by the user, this simultaneous push and pull may lead to inaccurate stent positioning, shortening or lengthening of the stent, or possibly even damage to the stent or target vessel. Another disadvantage of pin and pull systems is that there can be a lack of control on the deployment because the force to deploy the stent decreases as more of the stent is deployed. If the user maintains the same high force during deployment, the stent may be deployed too fast for the user to control. Another potential problem relates to building up tension in the outer sheath prior to movements thereof during the deployment process. If the user pauses during the deployment and releases this built up tension, deployment errors can occur when the user resumes tension to again move the outer sheath to the deployment position fully uncovering the self explaining stent.

The present disclosure is directed toward one or more of the problems set forth above.

SUMMARY OF THE DISCLOSURE

In one aspect, a vascular intervention device delivery system includes a thumbwheel rotatably mounted in a handle. The thumbwheel has a radially outward thumb surface and a radially inward ratchet surface of a ratchet. A catheter has a proximal end attached to the handle, and includes a distal carrier segment for mounting a vascular intervention device thereon. A retractable sheath is movable from a first position covering the distal carrier segment to a second position retracted proximally uncovering the distal carrier segment. A pull extends between the thumbwheel and the retractable sheath. A ratchet pawl of the ratchet is mounted in the handle and has a catch in contact with the ratchet surface. The ratchet holds the thumbwheel against rotation in a forward direction, and that the retractable sheath moves responsive to rotation of the thumbwheel in a reverse direction.

In another aspect, a method of operating a vascular intervention device delivery system includes rotating the thumbwheel in the reverse direction to build up tension in the retractable sheath and pull without moving the retractable sheath relative to the distal carrier segment of the catheter. A portion, which is less than all, of the distal carrier segment is uncovered by continuing to rotate the thumbwheel in the reverse direction. Rotation of the thumbwheel is paused in the reverse direction. Tension in the pull and the retractable sheath is maintained by stopping the ratchet and preventing rotation of the thumbwheel in the forward direction. A remaining portion of the distal carrier segment is then uncovered by resuming rotation of the thumbwheel in the reverse direction.

DETAILED DESCRIPTION

Figure 1:
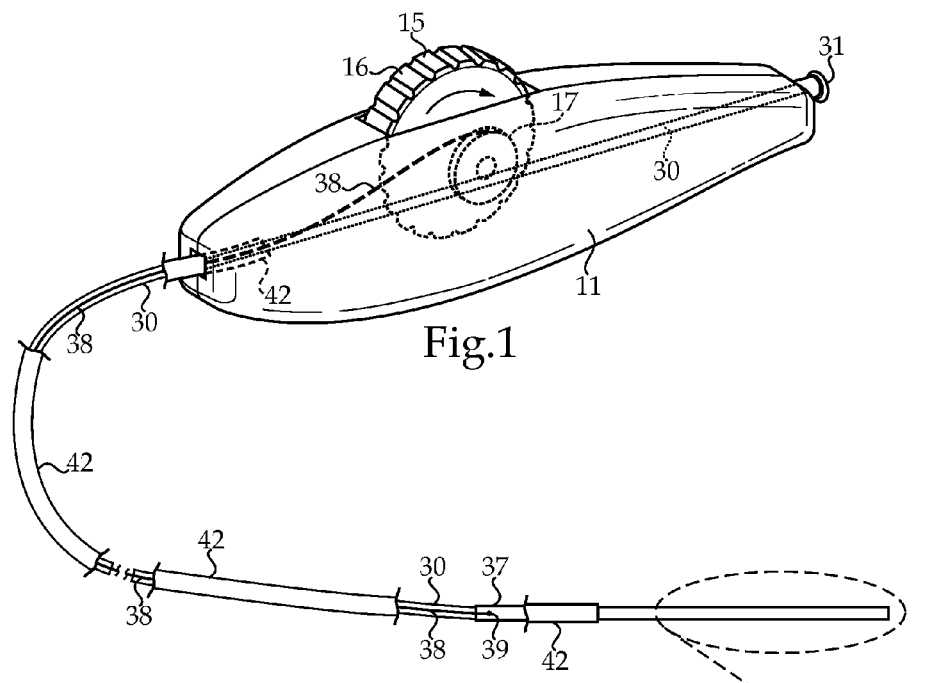
FIG. 1 is a perspective schematic view of a vascular intervention device delivery system according to the present disclosure.
Figure 2:
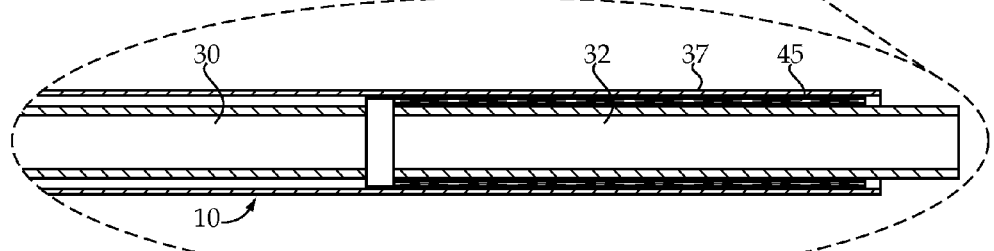
FIG. 2 is an enlarged view of the distal segment of the delivery system shown outlined with a dashed line in FIG. 1.
Figure 3:
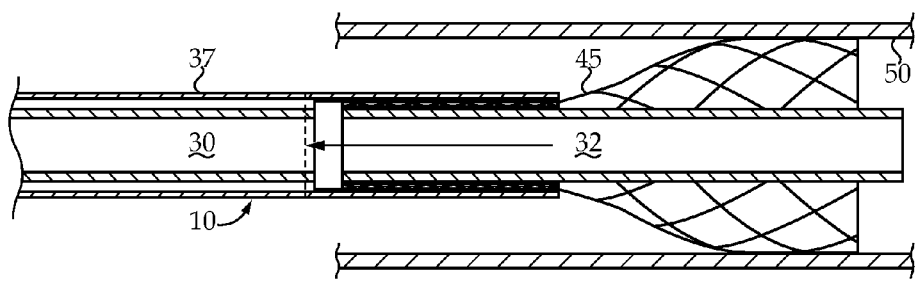
FIG. 3 is a view similar to FIG. 2 about half way through a deployment of a self expanding stent.

Referring to FIGS. 1-3, a vascular intervention device delivery system 10 is shown before and during delivery of a self expanding stent 45 into the vessel 50 of a patient. Delivery system 10 includes a handle 11 that may be gripped in one hand by a user during a delivery procedure. Handle 11 may, for instance, be manufactured from a suitable molded plastic, such as in two longitudinal halves that are joined in any suitable manner to form the complete handle 11. A thumbwheel 15 is rotatably mounted in the handle 11 and has a radially outward thumb surface 16 and a spool 17. A catheter 30 has a proximal end 31 attached to handle 11, and a distal carrier segment 32 for mounting a vascular intervention device, such as a self expanding stent 45, thereon. Proximal end 31 may take the form a Luer lock fitting so that treatment fluids or the like may be injected through catheter 30 in a manner well known in the art. A retractable sheath 37 is movable with respect to catheter 30 from a first position covering the distal carrier segment 32 to a second position indicated by the dashed line in FIG. 3 at which the retractable sheath 37 has been retracted proximally to uncover the distal carrier segment 32. FIG. 3 shows the retractable sheath 37 about half way between the first position and the second position.

A pull 38 extends between the spool 17 of thumbwheel 15 and the retractable sheath 37. Pull 38, which preferably is less elastic than the retractable sheath 37, may be attached to retractable sheath 37 at an attachment 39 in any manner known in the art. In most versions of the vascular intervention device delivery system 10 of the present disclosure, pull 38 will be longer than retractable sheath 37. Nevertheless, retractable sheath 37 could be longer than pull 38 without departing from the present disclosure. Pull 38 may comprise a metallic wire or thin band of metal.

A wire retention/stability sheath 42 surrounds a majority of the length of pull 38, and serves to keep pull 38 in close proximity to the outer surface of catheter 30 over much of the length of delivery system 10. Wire retention/stability sheath 42 may be unattached to catheter 30, pull 38 or retractable sheath 37, but may be attached to move with pull 38 and/or retractable sheath 37. On the other hand, wire retention/stability sheath 42 may be attached to catheter 30 at one or more locations so that pull 38 and retractable sheath 37 also move with respect to wire retention/stability sheath 42 during the delivery process. Wire retention/stability sheath 42 may terminate at its proximal end at a fixation point within handle 11.

When in its pre-deployment configuration, as shown in FIGS. 1 and 2, a vascular intervention device, such as a self expanding stent 45, is disposed between an outer surface of the distal carrier segment 32 of catheter 30, and an inner surface of the retractable sheath 37. During a typical procedure, the distal carrier segment 32 is positioned at a treatment location within a vessel 50 of a patient. After achieving proper positioning, the user then grips handle 11 and begins to rotate thumbwheel 15 so that pull 38 is wound onto spool 17. As this occurs, pull 38 and retractable sheath 37 move proximally with respect to catheter 30 to allow the self expanding stent 45 to expand away from carrier segment 32 and into contact with the inner wall of vessel 50 in a manner well known in the art. During this process, catheter 30 is placed in compression while both pull 38 and retractable sheath 37 are in tension. According to the present disclosure, handle 11 and thumbwheel 15 include a structure that allows thumbwheel 16 to rotate to wind pull 38 onto spool 17, but prevent rotation in an opposite direction. This aspect of the disclosure allows the user to stop the deployment procedure while retaining the stored elastic energy in pull 38 and retractable sheath 37.

Figure 4:
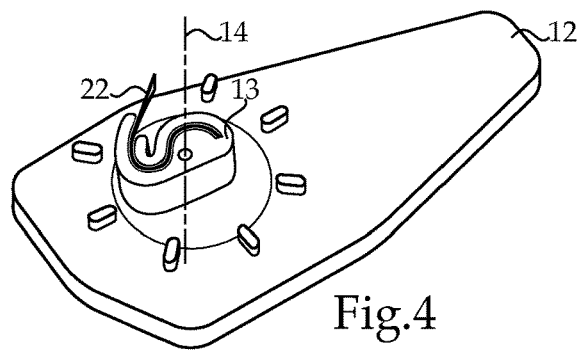
FIG. 4 is a perspective view of an assembly plate for the handle shown in FIG. 1.
Figure 5:
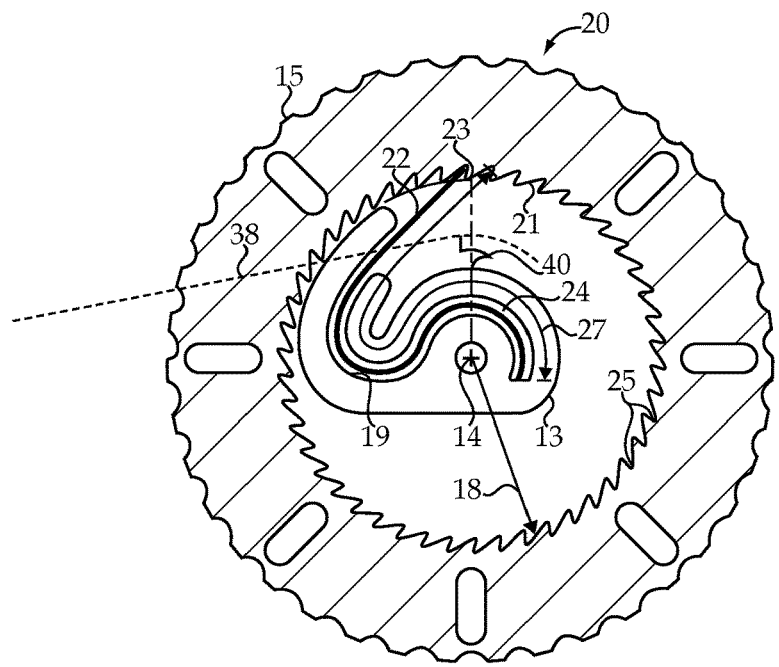
FIG. 5 is a partial sectioned view showing the ratchet according to the present disclosure.
Figure 6:
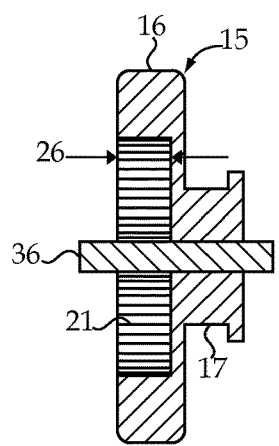
FIG. 6 is a sectioned side view through the thumbwheel of FIGS. 1 and 5.

Referring now in addition to FIGS. 4-6, a ratchet 20 provides the structure that prevents thumbwheel 16 from rotating in a forward direction. In particular, handle 11 may be formed to include, or have attached to an inner surface, an assembly plate 12 that defines a hub 13 that receives an axle 36 upon which thumbwheel 16 is rotatably mounted to rotate about axis 14 in a reverse direction permitted by ratchet 20. Thumbwheel 15 includes a radially inward ratchet surface 31 of ratchet 20. A ratchet pawl 22 of ratchet 20 is mounted in the handle 11, and has a catch 23 in contact with ratchet surface 21 of thumbwheel 15. Ratchet 20 holds thumbwheel 15 against rotation in a forward direction, but the retractable sheath 37 moves responsive to rotation of the thumbwheel 15 in a reverse direction.

In the illustrated embodiment, catch 23 takes the form of a deformed rectangular shaped band of spring steel 24 that is received in an S-shaped groove 19 defined by assembly plate 12 and oriented parallel to axis 14. The ratchet surface 21 of thumbwheel 15 may define a plurality of stops 25 in each of four 90° rotation angles. In the specific embodiment shown, ratchet surface 21 defines at least fifty stops 25 per revolution of thumbwheel 15 in order to provide the user with precise tactile control over the delivery procedure. The deformed band of spring steel 24 may have a width that contacts the ratchet surface 21 across the width 26. In addition, although not necessary, the deformed band of spring steel 24 may have a length 27 that is greater than radius 18 of thumbwheel 15. An imaginary line 40 that extends parallel from an end 28 of catch 23 to the axis 14 may be configured to be orthogonal to pull 38 where pull 38 contacts spool 37, as best shown in FIG. 5.

Figure 7:
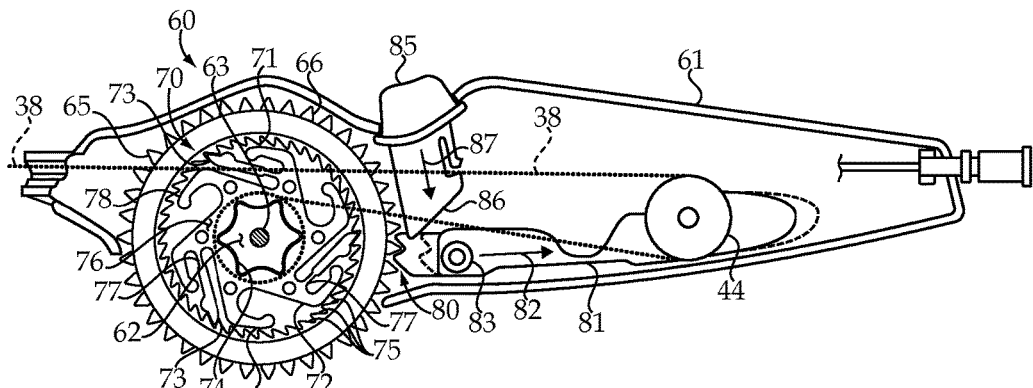
FIG. 7 is a sectioned side view of a handle portion of a vascular intervention device delivery system according to another aspect of the present disclosure.
Figure 8:
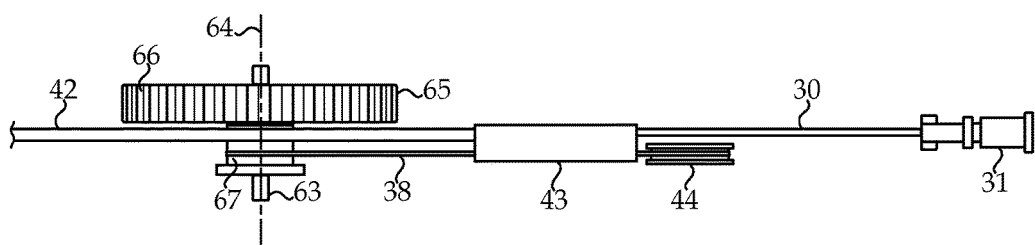
FIG. 8 is a top view of the inner workings of the vascular intervention device delivery system of FIG. 7, minus the handle.
Figure 9:
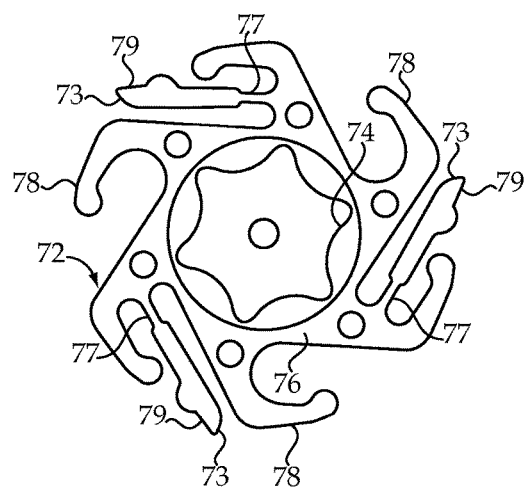
FIG. 9 is a side view of a ratchet pawl for the vascular intervention device delivery system of FIG. 7.

Referring now to FIGS. 7-9, a vascular intervention device delivery system 60 according to another aspect includes a ratchet 70 and a handle 71 with a structure that differs from that shown in relation to FIGS. 4-6. However, where similar numbers are used, those features correspond to similar features shown in FIGS. 1-3. Vascular intervention device delivery system 60 differs from the system 10 described earlier by the shape and structure of the ratchet pawl 72 and by the inclusion of a lock 80. Like the earlier version, ratchet 70 provides a structure that prevents thumbwheel 66 from rotating in a forward direction.

Handle 61 may be formed from a suitable plastic to include a key shaped hub 62 that is received in a matching key shaped opening 74 defined by ratchet pawl 72. This configuration permits assembly of ratchet pawl 72 to key shaped hub 62 in a plurality of different but equivalent angular orientations. Key shaped hub 72 may define a central opening that receives an axle 63 to define an axis 64 about which thumbwheel 65 rotates. Thumbwheel 65 includes a radially outward thumb surface 66 and a radially inward ratchet surface 71. Thumbwheel 65 may also include a spool 67 upon which the pull 38 is wound when the device delivery system 60 is operated. In this version, the wire retention/stability sheath 42 terminates at a junction box 43 (not shown in FIG. 7 for the sake of clarity) positioned within handle 61. As in the previous version, the pull 38 is positioned within the wire retention/stability sheath 42 and emerges from the junction box 43 to wrap around an idler wheel 44 and return in the reverse direction for being wound onto spool 67 as best shown in FIGS. 7 and 8. As in the previous embodiment, ratchet 70 prevents thumbwheel 65 from rotating in a forward direction, but the retractable sheath 37 (FIGS. 1-3) moves responsive to rotation of thumbwheel 65 in a reverse direction.

In this embodiment, catch 73 takes the form of spiral arms 79 that are attached to a central body 76 by living hinges 77. Unlike the ratchet pawl 22 shown in the embodiment in FIGS. 4-6, ratchet pawl 72 may most conveniently be formed of a suitable plastic material. When thumbwheel 65 is rotated in a reverse direction, each of the three catches 73 will click and be received into respective stops 75 that define ratchet surface 71. In this embodiment, ratchet catches 73 are equally distributed 120° apart around the axis 64 defined by axle 63. Thus, the three catches 73 will simultaneously contact the ratchet surface 71 at three different locations located 120° apart about axis 64. Those skilled in the art will appreciate that a ratchet pawl 72 having two, four or more catches 73 would also fall within the intended scope of this disclosure.

As best shown in FIGS. 7 and 9, the ratchet pawl 72 includes curved arms 78 that are distributed to provide a circular guide for the thumbwheel as the ratchet teeth rotate around the fixed ratchet. Thus, in some embodiments, the use of curved arms 78 could permit omission of axle 63 as shown, since the thumbwheel would rotate about axis 64 with the curved arms 78 contacting ratchet surface 71, even without the inclusion of axle 63. It is also worth noting that this embodiment differs from the earlier embodiment in that both the ratchet pawl 72 and the ratchet surface 71 of thumbwheel 65 may be made out of plastic, as opposed to a metal ratchet pawl 22 acting on a plastic ratchet surface 21 as in the earlier embodiment. By making both the pawl and the ratchet surface from the same material, the potential creation of the debris caused by the interaction of metal with plastic can be avoided.

In addition to ratchet 70, vascular intervention device delivery system 60 includes a lock 80 that allows thumbwheel 65 to be disabled during shipment and during positioning of the distal carrier segment 32 (FIGS. 1-3) at a treatment location within a patient. The lock 80 is movable between a locked position, as shown, and an unlocked position shown by dashed lines. The lock 80 includes a latch 81 positioned in handle 61 and movable along a line 82 between the locked position at which the latch 81 engages the radially outward thumb surface 66 of thumbwheel 65, and the unlocked position at which the latch 81 is out of contact with the radially outward thumb surface 66. Lock 80 also includes a pusher 85 that is at least partially positioned outside of handle 61, but on an opposite side of handle 61 from the exposed portion of thumbwheel 65. The pusher may include a wedge 86 that engages a post 83 of latch 81. Post 83 may be oriented perpendicular to the line 82 of action of latch 81. Vascular intervention device delivery system may be enabled by depressing pusher 85 along line 87 to move latch 81 out of contact with radially outward thumb surface 66 of thumbwheel 65.

INDUSTRIAL APPLICABILITY

The present disclosure is generally applicable to vascular intervention device delivery systems, and more particularly to a delivery system for delivery of self expanding stents and other vascular intervention devices with self expanding action. The present disclosure finds specific applicability to delivery of relatively long vascular intervention devices that produce substantial friction on the inner surface of retractable sheath 37, and thus require higher forces on retractable sheath 37 and pull 38 in order to successfully deliver the vascular intervention device to an intended treatment site.

The vascular intervention device delivery system 10, 60 will typically be packaged in a conventional sterile packaging in a known manner for shipment. After a wire guide (not shown) has been positioned in a patient's body across a treatment location, the catheter 30 may be slid over the wire guide to position the distal carrier segment 32 and the attached self expanding stent 45 at the treatment location within the vessel 50 of the patient. Thereafter, the wire guide may be withdrawn or left in place. During this portion of the procedure, the thumbwheel 65 of the vascular intervention device delivery system 60 may be disabled by maintaining the lock 80 in its locked position as shown in FIG. 7. After the distal carrier segment 32 is properly positioned and it is now time to deploy the self expanding stent 45, the user may depress pusher 85 to disengage lock 80 and move latch 81 out of contact with the radially outward thumb surface 66 of thumbwheel 65.

A method of operating vascular intervention device delivery system 10, 60 includes rotating the thumbwheel 15, 65 in a reverse direction to wind pull 38 onto spool 17, 67 to build up tension in the retractable sheath 37 and pull 38 without moving the retractable sheath 37 relative to the distal carrier segment 32 of catheter 30. The "reverse direction" is clockwise for the embodiment of FIG. 1 and counterclockwise for the embodiment of FIG. 7. Next, a portion, which is less than all, of the distal carrier segment 32 is uncovered by continuing to rotate the thumbwheel 15, 65 in the reverse direction. At some point during the delivery procedure, the user may then pause rotation of the thumbwheel 15, 65 in the reverse direction. For instance, the user may pause in order to confirm that the vascular intervention device, such as a self expanding stent 45, is being delivered to the desired location in the vessel 50 of the patient. While the rotation of the thumbwheel 15, 65 is paused, tension in the pull 38 and the retractable sheath 37 is maintained by holding the ratchet 20, 70 and preventing rotation of the thumbwheel 15, 65 in the forward direction. Ratchet 20, 70 may be considered to be in a hold configuration when catches 23, 73 are received in one of the stops 25, 75 of the ratchet surface 21, 71. A remaining portion of the distal carrier segment 32 is then uncovered to facilitate complete deployment of the self expanding stent 45 by resuming rotation of the thumbwheel 15, 65 in the reverse direction until retractable sheath 37 arrives at its second position fully uncovering distal carrier segment 32.

An important aspect of the ratchet operated vascular intervention device delivery system 10, 60 of the present disclosure is to allow for rotation of thumbwheel 15, 65 in one direction only. This means that the pull 38 and hence the retractable sheath 37 can only be pulled proximally. If the thumbwheel 15, 65 were able to rotate in both directions, it could cause the pull 38 to slack and possibly jump out of the collection diameter of the spool 17, 67 on thumbwheel 15, 65. Also, by keeping the rotation of thumbwheel 15, 65 to one direction only, ratchet 20, 70 allows all of the energy already placed in the system 10, 60 by the user to be maintained. For example, if the user was to partially deploy a self expanding stent 45 that had a deployment force of 30N they will have to put effort into getting the stent to partially deploy. This effort could have caused the sheath 37 to stretch slightly and also the inner catheter 30 to compress slightly. If this energy were lost when the thumbwheel 15, 65 were released, it would mean that when the deployment was resumed from that point, the user would have to rotate the thumbwheel 15, 65 an amount in order to reestablish tension in the system 10, 60 again before the self expanding stent 45 would continue to deploy. This may be especially important in the case of deploying longer stents that require higher forces.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A vascular intervention device delivery system comprising:
   a handle;
   a thumbwheel rotatably mounted in the handle and having a radially outward facing thumb surface and a radially inward facing ratchet surface of a ratchet;
   a catheter with a proximal end attached to the handle, and a distal carrier segment for mounting a vascular intervention device thereon;
   a retractable sheath movable from a first position covering the distal carrier segment, and a second position retracted proximally uncovering the distal carrier segment; and
   a pull extending between the thumbwheel and the retractable sheath;
   a ratchet pawl of the ratchet being mounted in the handle and having a catch in contact with the ratchet surface, and wherein the ratchet pawl includes a non-circular key shaped central opening that receives a matching non-circular key shaped hub attached to the handle; and
   the ratchet locking the thumbwheel against rotation in a forward direction, and the retractable sheath moving responsive to rotation of the thumbwheel in a reverse direction; and wherein the catch is one of three catches of the ratchet pawl, and the three catches simultaneously contact the ratchet surface at three different locations.

2. The vascular intervention device delivery system of claim 1 including a lock movable between a locked position and an unlocked position;
   the lock includes a latch positioned in the handle and movable along a line between the locked position at which the latch engages the radially outward facing thumb surface, and the unlocked position at which the latch is out of contact with the radially outward facing thumb surface; and
   a pusher at least partially positioned outside the handle and being operably coupled to move the latch from the locked position to the unlocked position.

3. The vascular intervention device delivery system of claim 2 wherein the pusher includes a wedge that engages a post that is attached to the latch and oriented perpendicular to the line; and
   the latch moves toward the unlocked position responsive to pushing movement of the pusher into the handle.

4. The vascular intervention device delivery system of claim 1 including a stability sheath that terminates in a junction box positioned inside the handle, and the stability sheath surrounding a portion of the pull that extends distally from the handle; and
   wherein each of the three catches are attached to a central body of the ratchet pawl by a living hinge.

5. The vascular intervention device delivery system of claim 4 including a lock movable between a locked position and an unlocked position;
   the lock includes a latch positioned in the handle and movable along a line between the locked position at which the latch engages the radially outward facing thumb surface, and the unlocked position at which the latch is out of contact with the radially outward facing thumb surface; and
   a pusher at least partially positioned outside the handle and being operably coupled to move the latch from the locked position to the unlocked position.

6. The vascular intervention device delivery system of claim 1 including a stability sheath extending distally from the handle and surrounding a portion of the pull that extends distally from the handle; and
   wherein the ratchet surface defines at least fifty stops per revolution of the thumbwheel.

7. The vascular intervention device delivery of claim 1 including a self expanding stent positioned radially between the sheath and the distal carrier segment of the catheter; and
   a distal end of the pull is positioned distally of the handle.

8. The vascular intervention device delivery system of claim 7 including a lock movable between a locked position and an unlocked position;
   the lock includes a latch positioned in the handle and movable along a line between the locked position at which the latch engages the radially outward facing thumb surface, and the unlocked position at which the latch is out of contact with the radially outward facing thumb surface; and
   a pusher at least partially positioned outside the handle and being operably coupled to move the latch from the locked position to the unlocked position.

9. The vascular intervention device delivery system of claim 1 including an idler wheel about which the pull wraps to return in a reverse direction for being wound onto a spool of the thumbwheel; and
   the pull is a thin band of metal.

10. The vascular intervention device delivery system of claim 1 including a stability sheath extending distally from the handle and surrounding a portion of the pull that extends distally from the handle; and
    wherein the retractable sheath moves toward the second position responsive to rotation of the thumbwheel in the reverse direction.

11. The vascular intervention device delivery system of claim 1 including a stability sheath that terminates in a junction box positioned inside the handle; and
    wherein the pull extends proximally from the junction box, extends through the junction box, and extends distally from the junction box.

12. A method of operating a vascular intervention device delivery system that includes a thumbwheel rotatably mounted in the handle and having a radially outward facing thumb surface and a radially inward facing ratchet surface of a ratchet; a catheter with a proximal end attached to the handle, and a distal carrier segment for mounting a vascular intervention device thereon; a retractable sheath movable from a first position covering the distal carrier segment, and a second position retracted proximally uncovering the distal carrier segment; a pull extending between the thumbwheel and the retractable sheath and including a portion extending distally from the handle; a ratchet pawl of the ratchet being mounted in the housing and having a catch in contact with the ratchet surface, and wherein the ratchet pawl includes a non-circular key shaped central opening that receives a matching non-circular key shaped hub attached to the handle; and the ratchet locking thumbwheel against rotation in a forward direction, and the retractable sheath moving responsive to rotation of the thumbwheel in a reverse direction, and a stability sheath extending distally from the handle and surrounding the portion of the pull that extends distally from the handle, and the method comprising the steps of:
    rotating the thumbwheel in the reverse direction to build up tension in the sheath and pull without moving the sheath relative to the distal carrier segment of the catheter;
    uncovering a portion, which is less than all, of the distal carrier segment by continuing to rotate the thumbwheel in the reverse direction;
    pausing rotation of the thumbwheel in the reverse direction;
    maintaining tension in the pull and the sheath by locking the ratchet and preventing rotation of the thumbwheel in the forward direction; and
    uncovering a remaining portion of the distal carrier segment by resuming rotation of the thumbwheel in the reverse direction.

13. The method of claim 12 including a step of enabling operation of the thumbwheel by moving a lock from a locked position in contact with the radially outward facing thumb surface to an unlocked position out of contact with the radially outward oriented thumb surface.

14. The method of claim 13 wherein the step of moving a lock includes pushing a pusher into the handle to move a latch from engagement with the radially outward facing thumb surface to being out of contact with the radially outward facing thumb surface.

15. A vascular intervention device delivery system comprising:
    a handle;
    a thumbwheel rotatably mounted in the handle and having a radially outward facing thumb surface and a radially inward facing ratchet surface of a ratchet;

a catheter with a proximal end attached to the handle, and a distal carrier segment for mounting a vascular intervention device thereon;

a retractable sheath movable from a first position covering the distal carrier segment, and a second position retracted proximally uncovering the distal carrier segment; and a pull extending between the thumbwheel and the retractable sheath, and including a portion extending distally from the handle;

a ratchet pawl of the ratchet being mounted in the handle and having a catch in contact with the ratchet surface, and wherein the ratchet pawl includes a non-circular key shaped central opening that receives a matching non-circular key shaped hub attached to the handle;

the ratchet locking the thumbwheel against rotation in a forward direction, and the retractable sheath moving responsive to rotation of the thumbwheel in a reverse direction; and a stability sheath extending distally from the handle and surrounding the portion of the pull that extends distally from the handle.

16. The vascular intervention device delivery system of claim 15 wherein a distal end of the pull is attached to the retractable sheath at an attachment.

17. The vascular intervention device delivery system of claim 16 wherein the stability sheath extends distally beyond the attachment.

18. The vascular intervention device delivery system of claim 17 wherein the pull is a thin band of metal.

19. The vascular intervention device delivery system of claim 18 including a lock that moves out of contact with the radially outward facing thumb surface responsive to pushing movement of a pusher into the handle.

20. The vascular intervention device delivery system of claim 19 wherein the stability sheath terminates at one end in a junction box positioned inside the handle; and the pull extends proximally from, through and distally from the junction box.

21. The vascular intervention device delivery system of claim 15 wherein the ratchet pawl includes the non-circular key shaped central opening that receives the matching non-circular key shaped hub attached to the handle in one of a plurality of different but equivalent angular mating orientations.

\* \* \* \* \*